(12) United States Patent  
Forbes et al.

(10) Patent No.: US 7,122,538 B2
(45) Date of Patent: Oct. 17, 2006

(54) SULFONAMIDE DERIVATIVES AS ANTIPSYCHOTIC AGENTS

(75) Inventors: Ian Thomson Forbes, Harlow (GB); Andrew Derrick Gribble, Harlow (GB); Andrew P. Lightfoot, Harlow (GB); Andrew H. Payne, Harlow (GB)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 10/530,538

(22) PCT Filed: Oct. 6, 2003

(86) PCT No.: PCT/EP03/11174

§ 371 (c)(1),
(2), (4) Date: Sep. 27, 2005

(87) PCT Pub. No.: WO2004/031181

PCT Pub. Date: Apr. 15, 2004

(65) Prior Publication Data

US 2006/0063757 A1 Mar. 23, 2006

(30) Foreign Application Priority Data

Oct. 7, 2002 (GB) ................. 0223226.2
Oct. 7, 2002 (GB) ................. 0223236.1
Jun. 23, 2003 (GB) ................. 0314627.1

(51) Int. Cl.
C07D 223/16 (2006.01)
C07D 209/44 (2006.01)
A61K 31/55 (2006.01)
A61D 31/4035 (2006.01)

(52) U.S. Cl. ............... 514/217.01; 540/594; 548/467; 514/414

(58) Field of Classification Search ......... 514/217.01, 514/414; 540/594; 548/467
See application file for complete search history.

(56) References Cited

U.S. PATENT DOCUMENTS

2005/0222124 A1* 10/2005 Bromidge et al. ..... 514/217.02

FOREIGN PATENT DOCUMENTS

| DE | 10053799 A | 5/2002 |
| EP | 0 007 070 A | 1/1980 |
| WO | WO0132646 A | 5/2001 |
| WO | WO0145694 A | 6/2001 |
| WO | WO03068752 A | 8/2003 |

* cited by examiner

*Primary Examiner*—Kamal A. Saeed
*Assistant Examiner*—Michael P. Barker
(74) *Attorney, Agent, or Firm*—James M. Kanagy; Stephen Venetianer; Charles M. Kinzig

(57) ABSTRACT

The invention provides compounds of formula (I):

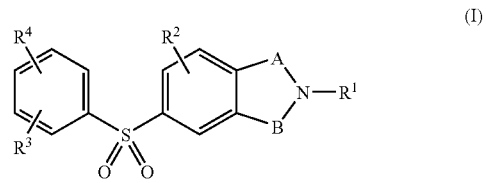

wherein
A and B represent the groups —$(CH_2)_m$— and —$(CH_2)_n$— respectively;
$R^1$ represents hydrogen or $C_{1-6}$alkyl;
$R^2$ represents hydrogen, halogen, hydroxy, cyano, nitro, hydroxy$C_{1-6}$alkyl, trifluoromethyl, trifluoromethoxy, $C_{1-6}$alkyl, $C_{1-6}$alkoxy, $C_{1-6}$fluoroalkoxy, —$(CH_2)_pC_{3-6}$cycloalkyl, —$(CH_2)_pOC_{3-6}$cycloalkyl, —$COC_{1-6}$alkyl, —$SO_2C_{1-6}$alkyl, —$SOC_{1-6}$alkyl, —S—$C_{1-6}$alkyl, —$CO_2C_{1-6}$alkyl, —$CO_2NR^5R^6$, —$SO_2NR^5R^6$, —$(CH_2)NR^5R^6$, —$(CH_2)_pNR^5COR^6$, optionally substituted aryl ring, optionally substituted heteroaryl ring or optionally substituted heterocyclyl ring;
$R^3$ represents hydrogen, halogen, hydroxy, cyano, nitro, hydroxy$C_{1-6}$alkyl, trifluoromethyl, trifluoromethoxy, $C_{1-6}$alkyl, $C_{1-6}$alkoxy, $C_{1-6}$fluoroalkoxy, —$(CH_2)_pC_{3-6}$cycloalkyl, —$(CH_2)_pOC_{3-6}$cycloalkyl, —$COC_{1-6}$alkyl, —$SO_2C_{1-6}$alkyl, —$SOC_{1-6}$alkyl, —S—$C_{1-6}$alkyl, —$CO_2C_{1-6}$alkyl, —$CO_2NR^7R^8$, —$SO_2NR^7R^8$, —$(CH_2)_p$ $NR^7R^8$ or —$(CH_2)_pNR^7COR^8$;
$R^4$ represents hydrogen, hydroxy, $C_{1-6}$alkyl, $C_{1-6}$alkoxy, $C_{1-6}$fluoroalkoxy, trifluoromethyl, trifluoromethoxy, halogen, —$OSO_2CF_3$, —$(CH_2)_pC_{3-6}$cycloalkyl, —$(CH_2)_qOC_{1-6}$alkyl or —$(CH_2)_pOC_{3-6}$cycloalkyl;
$R^5$ and $R^6$ each independently represent hydrogen, $C_{1-6}$alkyl or, together with the nitrogen or other atoms to which they are attached, form an azacycloalkyl ring or an oxo-substituted azacycloalkyl ring;
$R^7$ and $R^8$ each independently represent hydrogen or $C_{1-6}$alkyl;
m and n independently represent an integer selected from 1 and 2;
p independently represents an integer selected from 0, 1, 2 and 3;
q independently represents an integer selected from 1, 2 and 3;
or a pharmaceutically acceptable salt or solvate thereof, with the proviso that the compounds 8-hydroxy-3-methyl-7-phenylsulfonyl-2,3,4,5-tetrahydro-1H-3-benzazepine, 8-hydroxy-7-4-(hydroxyphenyl)sulfonyl-2,3,4,5-tetrahydro-1H-3-benzazepine, 7-phenylsulfonyl-1,2,3,4-tetrahydroisoquinoline and 7-phenylsulfonyl-1,2,3,4-tetrahydroisoquinoline hydrochloride are excluded.

The compounds are useful in therapy, in particular as antipsychotic agents.

3 Claims, No Drawings

SULFONAMIDE DERIVATIVES AS ANTIPSYCHOTIC AGENTS

This application is a 371 National Phase entry of international application PCT/EP03/011174 filed Oct. 6, 2003.

This invention relates to novel compounds, pharmaceutical compositions containing them and their use in therapy, in particular as antipsychotic agents.

U.S. Pat. No. 5,684,195 discloses a method of preparing sulfonamides of the formula

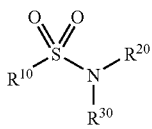

wherein $R^{10}$ represents, inter alia, an optionally substituted 5- or 6-membered heteroaryl, $R^{20}$ represents, inter alia, tetrahydroisoquinolinyl and $R^{30}$ represents, inter alia, hydrogen or $C_{1-6}$alkyl. In U.S. Pat. No. 5,684,195, it is stated that sulfonamides in general have been widely used for the treatment of bacterial or viral infections and are also found in drugs such as diuretics, hypoglycemic and antimalarial agents amongst others.

According to the invention, there is provided a compound of formula (I):

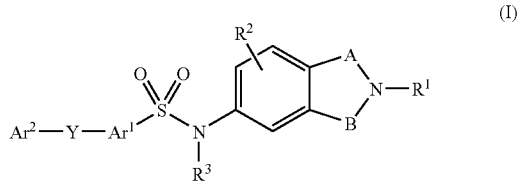

wherein
A and B represent the groups —$(CH_2)_m$— and —$(CH_2)_m$— respectively;
$R^1$ represents $C_{1-6}$alkyl;
$R^2$ represents hydrogen, halogen, hydroxy, cyano, nitro, hydroxy$C_{1-6}$alkyl, trifluoromethyl, trifluoromethoxy, $C_{1-6}$alkyl, $C_{1-6}$alkoxy, —$(CH_2)_pC_{3-6}$cycloalkyl, —$(CH_2)_p$O$C_{3-6}$cycloalkyl, —CO$C_{1-6}$alkyl, —SO$_2C_{1-6}$alkyl, —SO$C_{1-6}$alkyl, —S—$C_{1-6}$alkyl, —CO$_2C_{1-6}$alkyl, —CO$_2$NR$^4$R$^5$, —SO$_2$NR$^4$R$^5$, —(CH$_2$)$_p$NR$^4$R$^5$, —(CH$_2$)$_p$NR$^4$COR$^5$, an optionally substituted aryl group, an optionally substituted heteroaryl group or an optionally substituted heterocyclyl group;
$R^3$ represents hydrogen or $C_{1-6}$alkyl;
$Ar^1$ represents an optionally substituted heteroaryl group;
$Ar^2$ represents an optionally substituted phenyl or an optionally substituted heteroaryl group;
Y represents a bond, —O—, —$C_{1-6}$alkyl-, —CR$^6$R$^7$X—, —XCR$^6$R$^7$—, —NR$^8$CO— or —CONR$^8$—;
X represents oxygen, sulfur, —SO— or —SO$_2$—;
$R^4$ and $R^5$ each independently represent hydrogen or $C_{1-6}$alkyl or, together with the nitrogen or other atoms to which they are attached, form an azacycloalkyl ring or an oxo-substituted azacycloalkyl ring;
$R^6$ and $R^7$ each independently represent hydrogen, $C_{1-6}$alkyl or fluoro;
$R^8$ represents hydrogen or $C_{1-6}$alkyl;
m and n independently represent an integer selected from 1 and 2;
p independently represents an integer selected from 0, 1, 2 and 3;
or a pharmaceutically acceptable salt, solvate or pharmaceutically acceptable derivative thereof.

In a first aspect of the invention, there is provided a compound of the formula (I) as defined above with the proviso that when m represents 1 and n represents 2 or m represents 2 and n represents 1 and $R^2$ represents halogen, $C_{1-6}$alkyl or $_{1-6}$alkoxy, Y is other than a bond.

It is to be understood that the present invention covers all combinations of particular and preferred groups described herein above.

As used herein, the term "alkyl", either alone or as part of another group, refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "cycloalkyl" refers to a non-aromatic hydrocarbon ring containing the specified number of carbon atoms. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{6-7}$cycloalkyl group is preferred.

As used herein, the term "halogen" refers to the elements fluorine, chlorine, bromine and iodine. Preferred halogens are fluorine, chlorine and bromine.

As used herein, the term "aryl" refers to a phenyl or a naphthyl ring.

As used herein, the term "heteroaryl" refers to a 5- or 6-membered heterocyclic aromatic ring or a fused bicyclic heteroaromatic ring system.

As used herein, the term "heterocyclyl" refers to a 3- to 7-membered monocyclic saturated ring containing at least one heteroatom independently selected from oxygen, nitrogen and sulfur. Examples of suitable heterocyclic rings include, but are not limited to, piperidine and morpholine.

As used herein, the term "5 or 6-membered heterocyclic aromatic ring" refers to a monocyclic unsaturated ring containing at least one heteroatom independently selected from oxygen, nitrogen and sulfur. Examples of suitable 5- and 6-membered heterocyclic aromatic rings include, but are not limited to, furyl, thienyl, pyrrolyl, oxazolyl, thiazolyl, imidazolyl, oxadiazolyl, thiadiazolyl, pyridyl, triazolyl, triazinyl, pyridazyl, pyrimidinyl, pyrazolyl, isothiazolyl and isoxazolyl.

As used herein, the term "fused bicyclic heteroaromatic ring system" refers to a ring system comprising one six-membered unsaturated ring and one 5- or 6-membered unsaturated ring fused together, the ring system containing at least one heteroatom independently selected from oxygen, nitrogen and sulfur. Examples of suitable fused bicyclic heteroaromatic ring systems include, but are not limited to, indolyl, indolinyl, benzofuranyl, benzothienyl, quinolyl, isoquinolyl, tetrahydroquinolyl, benzodioxanyl, indanyl and tetrahydronapthyl.

As used herein, the term "azacycloalkyl ring" refers to a 4- to 7-membered monocyclic saturated ring containing one nitrogen atom. Examples of suitable azacycloalkyl rings are azetidine, pyrrolidine, piperidine and azepine.

As used herein, the term "oxo-substituted azacycloalkyl ring" refers to an azacycloalkyl ring as defined above substituted by one oxo group. Examples of suitable oxo-substituted azacycloalkyl rings include, but are not limited to, azetidinone, pyrrolidinone, piperidinone and azepinone.

As used herein, the term "optionally substituted" refers to optional substitution with the named substituent or substituents, multiple degrees of substitution being allowed unless otherwise stated.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

As used herein "pharmaceutically acceptable derivative" includes any pharmaceutically acceptable salt, solvate, ester or salt of such ester of a compound of formula (I) which, upon administration to the recipient is capable of providing (directly or indirectly) a compound of formula (I) or an active metabolite or residue thereof.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Most preferably the solvent used is water and the solvate may also be referred to as a hydrate.

It will be appreciated that for use in medicine the salts of formula (I) should be pharmaceutically acceptable. Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, malic, mandelic, acetic, fumaric, glutamic, lactic, citric, tartaric, benzoic, benzenesulfonic, p-toluenesulfonic, methanesulfonic or naphthalenesulfonic acid. Other non-pharmaceutically acceptable salts e.g. oxalates, may be used, for example in the isolation of compounds of formula (I) and are included within the scope of this invention. Also included within the scope of the invention are solvates and hydrates of the compounds of formula (I).

Certain of the compounds of formula (I) may form acid addition salts with one or more equivalents of the acid. The present invention includes within its scope all possible stoichiometric and non-stoichiometric forms thereof.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

Preferably, $R^1$ represents $C_{1-4}$alkyl. More preferably, $R^1$ represents methyl, ethyl, n-propyl or isopropyl. Even more preferably, $R^1$ represents methyl.

The group $R^2$ may be located at any free position on its respective phenyl ring.

When $R^2$ represents an optionally substituted aryl group, an optionally substituted heteroaryl group or an optionally substituted heterocyclyl group, the optional substituents may be independently selected from $C_{1-6}$alkyl, $C_{1-6}$alkoxy, —$(CH_2)_p$NR$^4$R$^5$ wherein p, $R^4$ and $R^5$ are as hereinbefore defined, halogen, trifluoromethyl, trifluoromethoxy, cyano and —S—$C_{1-6}$alkyl. Preferably, the optional substituents are independently selected from chloro, fluoro, bromo, methyl, ethyl, t-butyl, methoxy, trifluoromethyl, trifluoromethoxy, cyano and —S-methyl.

Preferably, $R^2$ represents hydrogen, halogen, $C_{1-6}$alkyl, $C_{1-6}$alkoxy or —$(CH_2)_p$NR$^4$R$^5$ wherein p, $R^4$ and $R^5$ are as hereinbefore defined. More preferably, $R^2$ represents hydrogen, halogen, $C_{1-4}$alkyl, $C_{1-4}$alkoxy or dimethylamino. Even more preferably, $R^2$ represents hydrogen or methoxy.

Preferably, $R^3$ represents hydrogen or $C_{1-4}$alkyl. More preferably, $R^3$ represents hydrogen, methyl, ethyl, n-propyl or isopropyl. Even more preferably, $R^3$ represents hydrogen.

When $Ar^1$ represents an optionally substituted heteroaryl group, the optional substituents may be independently selected from $C_{1-6}$-alkyl, $C_{1-6}$alkoxy, halogen, trifluoromethyl, trifluoromethoxy, cyano and —S—$C_{1-6}$alkyl. Preferably, the optional substituents are independently selected from chloro, fluoro, methyl, methoxy, trifluoromethyl and trifluoromethoxy.

Preferably, $Ar^1$ is substituted by 0 to 3 substituents, more preferably 0, 1 or 2 substituents.

Preferably, $Ar^1$ represents optionally substituted thienyl.

Preferably, $Ar^1$ represents optionally substituted thienyl whereby one or more optional substituents are selected from halogen (such as chloro, e.g. 4-chloro, or fluoro, e.g. 4-fluoro, 2,4difluoro or 3,4-difluoro), $C_{1-6}$alkyl (such as methyl, e.g. 2-methyl), $C_{1-6}$alkoxy (such as methoxy, e.g. 3-methoxy or 4-methoxy), trifluoromethyl (e.g.3-trifluoromethyl or 4-trifluoromethyl) and trifluoromethoxy. Other examples of multiple optional substituents include, for example, 2-methyl-4-chloro. Even more preferably, $Ar^1$ represents unsubstituted thienyl.

When $Ar^2$ represents optionally substituted phenyl or an optionally substituted heteroaryl group, the optional substituents may be independently selected from $C_{1-6}$alkyl, $C_{1-6}$alkoxy, halogen, trifluoromethyl, trifluoromethoxy, cyano and —S—$C_{1-6}$alkyl. Preferably, the optional substituents are independently selected from chloro, fluoro, methyl, methoxy, trifluoromethyl and trifluoromethoxy.

Preferably, $Ar^2$ is substituted by 0 to 3 substituents, more preferably 1 or 2 substituents.

Preferably, $Ar^2$ represents optionally substituted phenyl, isoxazolyl, thiazolyl or thienyl. More preferably, $Ar^2$ represents optionally substituted phenyl.

Preferably, $Ar^2$ represents optionally substituted phenyl whereby one or more optional substituents are selected from halogen (such as chloro, e.g. 4-chloro, or fluoro, e.g. 4-fluoro, 2,4-difluoro or 3,4-difluoro), $C_{1-6}$alkoxy (such as methoxy, e.g. 3-methoxy or 4-methoxy), trifluoromethyl (e.g.3-trifluoromethyl or 4-trifluoromethyl) and trifluoromethoxy or $Ar^2$ represents optionally substituted thiazolyl whereby one or more optional substituents are selected from $C_{1-6}$alkyl (such as methyl, e.g. 2-methyl).

Preferably, $R^4$ and $R^5$ independently represent hydrogen or $C_{1-4}$alkyl. More preferably, $R^4$ and $R^5$ independently represent hydrogen or methyl.

Preferably, $R^6$ and $R^7$ independently represent hydrogen, fluoro or methyl. More preferably, $R^6$ and $R^7$ independently represent hydrogen.

Preferably, $R^8$ represents hydrogen or methyl. More preferably, $R^8$ represents hydrogen.

Preferably, p represents 0.

In a first aspect of the invention, there is provided a compound of formula (IA):

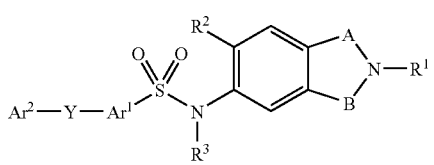

(IA)

or a pharmaceutically acceptable derivative thereof wherein groups A, B, $Ar^1$, $Ar^2$, Y and $R^1$ to $R^3$ have any of the meanings as given hereinbefore. For compounds of formula (IA), $R^2$ is preferably hydrogen or methoxy.

In a further aspect of the invention, there is provided a compound of the formula (IA) as defined above with the proviso that when m represents 1 and n represents 2 or m represents 2 and n represents 1 and $R^2$ represents halogen, $C_{1-6}$alkyl or $C_{1-6}$alkoxy, Y is other than a bond.

In a further aspect of the invention, Y is a bond and there is provided a compound of formula (IB):

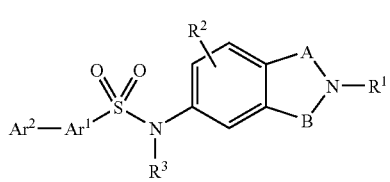

(IB)

or a pharmaceutically acceptable derivative thereof wherein groups A, B, $Ar^1$, $Ar^2$ and $R^1$ to $R^3$ have any of the meanings as given hereinbefore.

In a further aspect of the invention, there is provided a compound of the formula (IB) as defined above with the proviso that when m represents 1 and n represents 2 or m represents 2 and n represents 1, $R^2$ is other than halogen, $C_{1-6}$alkyl or $C_{1-6}$alkoxy.

In a further aspect of the invention, Y is a bond and there is provided a compound of formula (IC):

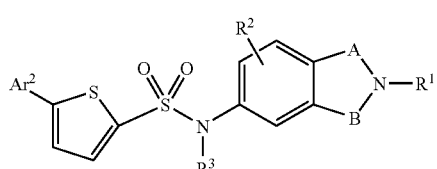

(IC)

or a pharmaceutically acceptable derivative thereof wherein the groups A, B, $Ar^2$ and $R^1$ to $R^3$ have any of the meanings as given hereinbefore.

In a further aspect of the invention, there is provided a compound of the formula (IC) as defined above with the proviso that when m represents 1 and n represents 2 or m represents 2 and n represents 1, $R^2$ is other than halogen, $C_{1-6}$alkyl or $C_{1-6}$alkoxy.

In a further aspect of the invention, Y is a bond and there is provided a compound of formula (ID):

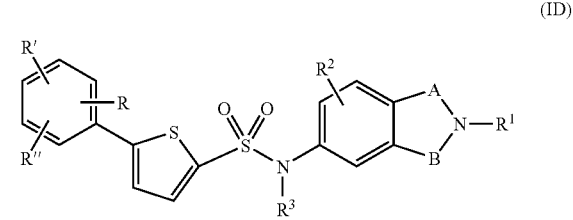

(ID)

or a pharmaceutically acceptable derivative thereof wherein groups A, B, $R^1$ to $R^3$ have any of the meanings as given hereinbefore and the groups R, R' and R" represent up to three optional substituents on the phenyl ring as defined hereinbefore for the group $Ar^2$.

In a further aspect of the invention, there is provided a compound of the formula (ID) as defined above with the proviso that when m represents 1 and n represents 2 or m represents 2 and n represents 1, $R^2$ represents halogen, $C_{1-6}$alkyl or $C_{1-6}$alkoxy.

In a further aspect of the invention, there is provided a compound of formula (IE):

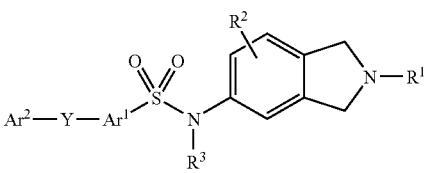

(IE)

or a pharmaceutically acceptable derivative thereof wherein groups $Ar^1$, $Ar^2$, Y and $R^1$ to $R^3$ have any of the meanings as given hereinbefore.

In a further aspect of the invention, there is provided a compound of formula (IF):

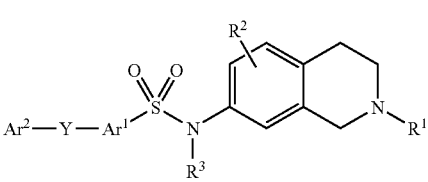

(IF)

or a pharmaceutically acceptable derivative thereof wherein groups $Ar^1$, $Ar^2$, Y and $R^1$ to $R^3$ have any of the meanings as given hereinbefore.

In a further aspect of the invention, there is provided a compound of the formula (IF) as defined above with the proviso that when $R^2$ represents halogen, $C_{1-6}$alkyl or $C_{1-6}$alkoxy, Y is other than a bond.

In another aspect of the invention, there is provided a compound of formula (IG):

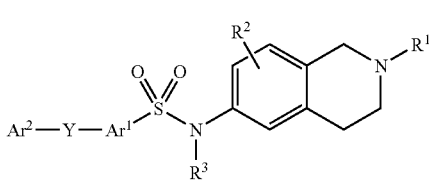

or a pharmaceutically acceptable derivative thereof wherein groups Ar¹, Ar², Y and R¹ to R³ have any of the meanings as given hereinbefore.

In a further aspect of the invention, there is provided a compound of the formula (IG) as defined above with the proviso that when $R^2$ represents halogen, $C_{1-6}$alkyl or $C_{1-6}$alkoxy, Y is other than a bond.

In another aspect of the invention, there is provided a compound of formula (IH):

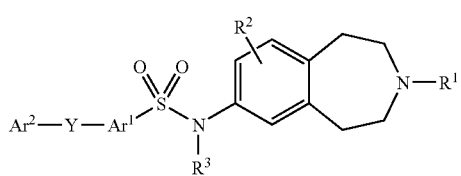

or a pharmaceutically acceptable derivative thereof wherein groups Ar¹, Ar², Y and R¹ to R³ have any of the meanings as given hereinbefore.

In another aspect of the invention, there is provided a compound of formula (IJ):

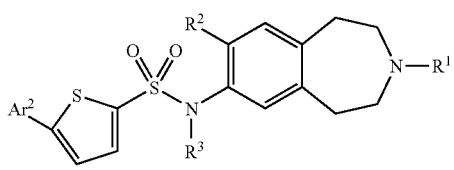

or a pharmaceutically acceptable derivative thereof wherein groups Ar² and R¹ to R³ have any of the meanings as given hereinbefore.

Particular compounds according to the invention include those incorporated in Table 1 and those specifically exemplified and named hereinafter:

5-(4-Chlorophenyl)-thiophene-2-sulfonic acid (8-methoxy-3-methyl-2,3,4,5-tetrahydro-1H-benzo[d]azepin-7-yl)amide;
5-(3-Methoxyphenyl)-thiophene-2-sulfonic acid(8-methoxy-3-methyl-2,3,4,5-tetrahydro-1H-benzo[d]azepin-7-yl)amide;
5-(4-Methoxyphenyl)-thiophene-2-sulfonic acid(8-methoxy-3-methyl-2,3,4,5-tetrahydro-1H-benzo[d]azepin-7-yl)amide;
5-(3,4-Difluorophenyl)-thiophene-2-sulfonic acid(8-methoxy-3-methyl-2,3,4,5-tetrahydro-1H-benzo[d]azepin-7-yl)amide;
5-(2,4-Difluorophenyl)-thiophene-2-sulfonic acid(8-methoxy-3-methyl-2,3,4,5-tetrahydro-1H-benzo[d]azepin-7-yl)amide;
5-(3-Chlorophenyl)-thiophene-2-sulfonic acid (8-methoxy-3-methyl-2,3,4,5-tetrahydro-1H-benzo[d]azepin-7-yl)amide;
5-(3-Fluorophenyl)-thiophene-2-sulfonic acid (8-methoxy-3-methyl-2,3,4,5-tetrahydro-1H-benzo[d]azepin-7-yl)amide;
5-(4-Trifluoromethylphenyl)-thiophene-2-sulfonic acid (8-methoxy-3-methyl-2,3,4,5-tetrahydro-1H-benzo[d]azepin-7-yl)amide;
5-(3-Trifluoromethylphenyl)-thiophene-2-sulfonic acid (8-methoxy-3-methyl-2,3,4,5-tetrahydro-1H-benzo[d]azepin-7-yl)amide;
5-(4-Fluorophenyl)-thiophene-2-sulfonic acid (8-methoxy-3-methyl-2,3,4,5-tetrahydro-1H-benzo[d]azepin-7-yl)amide;
5-(4-Fluorophenyl)-thiophene-2-sulfonic acid (3-methyl-2,3,4,5-tetrahydro-1H-benzo[d]azepin-7-yl)amide;
5-(4-Chlorophenyl)-thiophene-2-sulfonic acid (3-methyl-2,3,4,5-tetrahydro-1H-benzo[d]azepin-7-yl)amide;
5-Isoxazol-3-yl-thiophene-2-sulfonic acid (8-methoxy-3-methyl-2,3,4,5-tetrahydro-1H-benzo[d]azepin-7-yl)-amide;
5-(2-Methylthiazol-5-yl)-thiophene-2-sulfonic acid (8-methoxy-3-methyl-2,3,4,5-tetrahydro-1H-benzo[d]azepin-7-yl)-amide;
[2,3']Bithiophenyl-5-sulfonic acid (3-methyl-2,3,4,5-tetrahydro-1H-benzo[d]azepin-7-yl)-amide;
5-(4-Chlorophenyl)thiophene-2-sulfonic acid (8-dimethylamino-3-methyl-2,3,4,5-tetrahydro-1H-3-benzazepin-7-yl)amide;
5-(4-Fluorophenyl)thiophene-2-sulfonic acid (8-dimethylamino-3-methyl-2,3,4,5-tetrahydro-1H-3-benzazepin-7-yl)amide;
5-(2,4-Difluorophenyl)thiophene-2-sulfonic acid (8-dimethylamino-3-methyl-2,3,4,5-tetrahydro-1H-3-benzazepin-7-yl)amide; and
5-(3,4-Difluorophenyl)thiophene-2-sulfonic acid (8-dimethylamino-3-methyl-2,3,4,5-tetrahydro-1H-3-benzazepin-7-yl)amide.

These compounds may be in the form of their free base or pharmaceutically acceptable salts thereof, particularly the monohydrochloride salt.

The present invention also provides a general process (A) for preparing compounds of formula (I) which process comprises:

reacting a compound of formula (II)

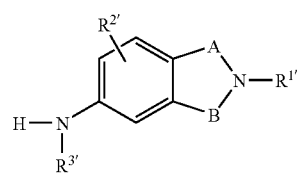

with a compound of formula (III)

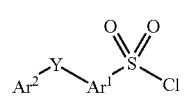

wherein $Ar^1$, $Ar^2$ and Y are as hereinbefore defined and $R^{1'}$—$R^{3'}$ represent $R^1$ to $R^3$ as hereinbefore defined or are groups that may be readily convertible to $R^1$ to $R^3$.

This general method (A) can be conveniently performed by mixing the two components in a solvent such as pyridine or dichloromethane (in the presence of a base), at 0° C.

The present invention also provides a general process (B) for preparing compounds of formula (I) wherein Y is a bond, which process comprises:

reacting a compound of formula (IV)

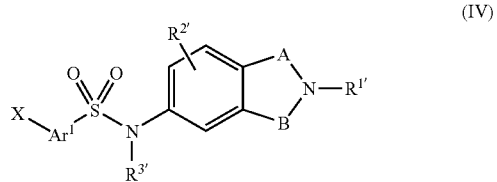

(IV)

with an aryl boronic acid of formula (V)

(V)

wherein X is a leaving group, such as iodo, bromo or triflate, $Ar^1$ and $Ar^2$ are as hereinbefore defined and $R^{1'}$—$R^{3'}$ represent $R^1$ to $R^3$ as hereinbefore defined or are groups that may be readily convertible to $R^1$ to $R^3$, under standard Suzuki conditions, e.g. treatment of compound (IV) with 4-chlorobenzeneboronic acid in toluene containing aqueous sodium carbonate and a catalytic amount of Pd $(PPh_3)_4$, at reflux under argon.

The present invention also provides a general process (C) for preparing compounds of formula (I) which process comprises:

converting a compound of formula (I)

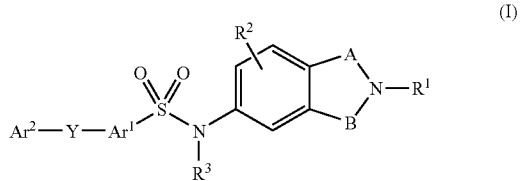

(I)

wherein A, B, $Ar^1$, $Ar^2$, Y and $R^1$ to $R^3$ are as hereinbefore defined, into another compound of formula (I) by substituting the group $R^1$ or the group $R^3$ using conventional techniques.

Interconversion of one of the $R^{1'}$ to $R^{3'}$ group to the corresponding $R^1$ to $R^3$ groups another typically arises when one compound of formula (I) is used as the immediate precursor of another compound of formula (I), or when it is easier to introduce a more complex or reactive substituent at the end of a synthetic sequence.

For example, conversion of $R^{1'}$ from a t-butoxycarbonyl (BOC) group to hydrogen is conducted by the treatment of the N-BOC protected compound with hydrogen chloride in ethanol or dioxan at room temperature.

Conversion of $R^{1'}$ from hydrogen to an alkyl group is conducted by the treatment of the sulfonamide NH compound with the appropriate aldehyde in dichloroethane in the presence of a reducing agent, such as sodium triacetoxyborohydride, or by the treatment of the NH compound with the appropriate alkyl halide, such as iodomethane, under standard alkylation conditions (potassium carbonate in DMF at 60° C.).

Conversion of $R^{3'}$ from hydrogen to an alkyl group is conducted by the treatment of the sulfonamide NH compound with the appropriate alcohol, such as methanol, under Mitsunobu conditions i.e. treatment with diisopropyl azodicarboxylate/triphenylphosphine and methanol in tetrahydrofuran at room temperature.

Compounds of formula (II) are known in the literature or may be prepared by known processes, for example, reduction of the corresponding nitro compound as disclosed in WO 99/14197, or by procedures analogous to these procedures. Suitable examples of an $R^{1'}$ protecting group are trifluoroacetyl or the t-butoxycarbonyl (BOC) group.

Compounds of formula (III) are commercially available or may be prepared by established procedures, for example chlorosulfonylation of a suitable substituted aromatic precursor, using chlorosulfonic acid, for example as described in J. Med. Chem., 2000, 43, 156–166.

Compounds of formula (IV) may be prepared from compounds of formula (II) by the treatment with the appropriate heteroaryl sulfonyl chloride using standard conditions, for example in pyridine or dichloromethane in the presence of a base such as triethylamine at room temperature.

Compounds of formula (V) are commercially available or may be prepared by known methodology, for example lithiation of a suitable substituted bromoheteroaryl at low temperature followed by quenching with tri-isopropylborate and acidic hydrolysis of the reaction product.

Compounds of formula (I) have been found to exhibit affinity for dopamine receptors, in particular the $D_3$ and $D_2$ receptors, and are useful in the treatment of disease states which require modulation of such receptors, such as psychotic conditions. Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the dopamine $D_3$ receptor may give rise to beneficial antipsychotic activity without significant eps. (see for example Sokoloff et al, Nature, 1990; 347: 146–151; and Schwartz et al, Clinical Neuropharmacology, Vol 16, No. 4, 295–314, 1993). Additionally, certain compounds of formula (I) have antagonist affinity for the serotonin $5-HT_{2A}$, $5-HT_{2C}$ and $5-HT_6$ receptors. These additional properties may give rise to enhanced anti-psychotic activity (e.g. improved effects on cognitive dysfunction) and/or reduced eps.

The compounds of formula (I) are of use as antipsychotic agents for example in the treatment of schizophrenia, schizoaffective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236–242). From the localisation of $D_3$ receptors, it could also be envisaged that the compounds could also have utility for the treatment of substance abuse where it has been suggested that D3 receptors are involved (e.g. see Levant, 1997, Pharmacol. Rev., 49, 231–252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, obesity, sexual dysfunction, sleep disorders, emesis, movement disorders, obsessive-compulsive disorders, amnesia, aggression, autism, vertigo, dementia, circadian rhythm disorders and gastric motility disorders e.g. iBS.

The invention also provides the use of a compound of formula (I) or a pharmaceutically acceptable derivative thereof in therapy.

The invention also provides a compound of formula (I) or a pharmaceutically acceptable derivative thereof for use in the treatment of a condition in a mammal for which modulation (especially antagonism/inhibition) of dopamine receptors (especially dopamine $D_3$ receptors) and/or serotonin receptors (especially $5-HT_6$, $5-HT_{2A}$ and $5-HT_{2C}$) is beneficial.

A preferred use for dopaminelserotonin antagonists according to the present invention is in the treatment of psychoses such as schizophrenia or in the treatment of substance abuse.

Therefore, also provided is a compound of formula (I) or a pharmaceutically acceptable derivative thereof for use in the treatment of a psychotic condition (e.g. schizophrenia) or substance abuse in a mammal.

The invention also provides the use of a compound of formula (I) or a pharmaceutically acceptable derivative thereof in the manufacture of a medicament for the treatment of a condition in a mammal for which modulation (especially antagonism/inhibition) of dopamine receptors (especially dopamine $D_3$ receptors) and/or serotonin receptors (especially $5-HT_6$, $5HT_{2A}$ and $5-HT_{2C}$) is beneficial.

Also provided is the use of a compound of formula (I) or a pharmaceutically acceptable derivative thereof in the manufacture of a medicament for the treatment of a psychotic condition (e.g. schizophrenia) or substance abuse in a mammal.

In a further aspect therefore the present invention provides a method of treating a condition for which modulation (especially antagonism/inhibition) of dopamine receptors (especially dopamine $D_3$ receptors) and/or serotonin receptors (especially $5-HT_6$, $5HT_{2A}$ and $5-HT_{2C}$) is beneficial, which comprises administering to a mammal (e.g. human) in need thereof an effective amount of a compound of formula (I) or a pharmaceutically (i.e. physiologically) acceptable derivative thereof. Such conditions in particular include psychoses/psychotic conditions such as schizophrenia, and substance abuse.

Thus, a still further aspect the invention provides a method of treating a psychotic condition (e.g. schizophrenia) or substance abuse which comprises administering to a mammal (e.g. human) in need thereof an effective amount of a compound of formula (I) as herein defined or a pharmaceutically acceptable derivative thereof.

Also provided is a compound of formula (I) or a pharmaceutically acceptable derivative thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e. physiologically) acceptable derivative thereof and a pharmaceutically (i.e. physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable derivatives which are active when given orally can be formulated as liquids or solids, for example syrups, suspensions or emulsions, tablets, capsules and lozenges.

A liquid formulation will generally consist of a suspension or solution of the compound or pharmaceutically acceptable derivative in a suitable liquid carrier(s) for example an aqueous-solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable derivative in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule. Each dosage unit for oral administration contains preferably from 1 to 250 mg (and for parenteral administration contains preferably from 0.1 to 25 mg) of a compound of the formula (I) or a pharmaceutically acceptable derivative thereof calculated as the free base.

The pharmaceutically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a pharmaceutically acceptable derivative thereof calculated as the free base, the compound being administered 1 to 4 times per day. Suitably the compounds will be administered for a period of continuous therapy, for example for a week or more.

Biological Test Methods

Binding Experiments on Cloned Dopamine (e.g. D2 and D3) Receptors

The ability of the compounds to bind selectively to human D2/D3 dopamine receptors can be demonstrated by measuring their binding to cloned receptors. The inhibition constants ($K_i$) of test compounds for displacement of [$^{125}$I]-Iodosulpride binding to human D2/D3 receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at $-80°$ C. Crude cell membranes were prepared by homogenisation followed by high-speed centrifugation, and characterisation of cloned receptors achieved by radioligand binding.

Preparation of CHO cell membranes: Cell pellets were gently thawed at room temperature, and resuspended in about 20 volumes of ice-cold Extraction buffer; 5 mM EDTA, 50 mM Trizma pre-set crystals (pH7.4@37° C.), 1 mM $MgCl_2$, 5 mM KCl and 120 mM NaCl. The suspension was homogenised using an Ultra-Turrax at full speed for 15 seconds. The homogenate was centrifuged at 18,000 r.p.m for 15 min at 4° C. in a Sorvall RC5C centrifuge. Supernatant was discarded, and homogenate re-suspended in extraction buffer then centrifugation was repeated. The final pellet was resuspended in 50 mM Trizma pre-set crystals (pH 7.4 @ 37° C.) and stored in 1 ml aliquot tubes at $-80°$ C. (D2=3.0E+08 cells, D3=7.0E+07 cells and D4=1.0E+08 cells). The protein content was determined using a BCA protocol and bovine serum albumin as a standard (Smith, P. K., et al., Measurement of protein using bicinchoninic acid. Anal. Biochem. 150, 76–85 (1985)).

Binding experiments: Crude D2/D3 cell membranes were incubated with 0.03 nM [$^{125}$I]-Iodosulpride (~2000 Ci/mmol; Amersham, U. K., and the test compound in a buffer containing 50 mM Trizma pre-set crystals (pH 7.4 @ 37° C.), 120 mM NaCl, 5 mM KCl, 2 mM $CaCl_2$, 1 mM $MgCl_2$, 0.3% (w/v) bovine serum albumin. The total volume is 0.2 ml and incubated in a water bath at 37° C. for 40 minutes. Following incubation, samples were filtered onto GF/B Unifilters using a Canberra Packard Filtermate, and washed four times with ice-cold 50 mM Trizma pre-set crystals (pH 7.4 @ 37° C.). The radioactivity on the filters was measured using a Canberra Packard Topcount Scintillation counter. Non-specific binding was defined with 10 μM SKF-102161 (YM-09151). For competition curves, 10 serial log concentrations of competing cold drug were used (Dilution range: 10 μM–10 pM). Competition curves were analysed using Inflexion, an iterative curve fitting programme in Excel. Results were expressed as $pK_i$ values where $pK_i = -\log_{10}[K_i]$.

The exemplified compounds have $pK_i$ values within the range of 7.4–8.9 at the dopamine $D_3$ receptor.

The exemplified compounds have $pK_i$ values within the range of 6.4–7.8 at the dopamine $D_2$ receptor.

Binding Experiments on Cloned 5-$HT_6$ Receptors

Compounds can be tested following the procedures outlined in WO 98/27081.

The exemplified compounds have $pK_i$ values within the range of 7.5–8.7 at the serotonin 5-$HT_6$ receptor.

Binding Experiments on Cloned 5-$HT_{2C}$ Receptors

Compounds can be tested following the procedures outlined in WO 94/04533 and *British Journal of Pharmacology* (1996) 117, 427–434.

The exemplified compounds have $pK_i$ values within the range of 5.7–7.5 at the serotonin 5-$HT_{2C}$ receptor.

Binding Experiments on Cloned 5-$HT_{2A}$ Receptors

Compounds can be tested following the procedures outlined in *British Journal of Pharmacology* (1996) 117, 427–434.

The exemplified compounds have $pK_i$ values within the range of 6.0–7.8 at the serotonin 5-$HT_{2A}$ receptor.

The invention is further illustrated by the following non-limiting examples:

DESCRIPTION 1

7-Amino-8-methoxy-1,2,4,5-tetrahydro-3-benzazepine-3-carboxylic acid tert-butyl ester (D1)

7-Hydroxy-1,2,4,5-tetrahydro-benzo[d]azepine-3-carboxylic acid tert-butyl ester (D1a)

7-Methoxy-2,3,4,5-tetrahydro-1H-3-benzazepine (10 g) in 48% aqueous hydrobromic acid (350 ml) was allowed to stir at 100° C. for 4 h. The mixture was allowed to cool to 20° C. then evaporated to dryness, giving the crude hydroxy compound as a brown solid (14.5 g). This solid was dissolved in tetrahydrofuran (100 ml) and water (70 ml) and triethylamine (8 g) was added dropwise, followed by a solution of di-tert-butyl dicarbonate (14 g) in tetrahydrofuran (20 ml). The resulting mixture was allowed to stir at 20° C. for 16 h then partitioned between ethyl acetate (200 ml) and water (200 ml). The aqueous layer was extracted with ethyl acetate (100 ml). The combined organic extracts were washed with saturated aqueous sodium bicarbonate (100 ml), dried over anhydrous sodium sulfate and evaporated to dryness. The resulting oil was purified by chromatography over silica gel, eluting with 10–30% ethyl acetate in hexane, affording the title compound D1a as a white solid (8 g), MS (API$^+$): Found 164 (MH$^+$-Boc). $C_{15}H_{21}NO_3$ requires 263. $^1$H NMR: δ CDCl$_3$ 1.48 (9H, s), 2.75–2.87 (4H, m), 3.40–3.60 (4H, m), 4.95 (1H, s), 6.50–6.62 (2H, m), 6.96 (1H, d).

7-Methoxy-1,2,4,5-tetrahydro-benzo[d]azepine-3-carboxylic acid tert-butyl ester (D1b)

Reaction of the phenol D1a with potassium carbonate/methyl iodide in dimethylformamide afforded the title compound. MH$^+$ 278.

7-Methoxy-8-nitro-1,2,4,5-tetrahydro-benzo[d]azepine-3-carboxylic acid tert-butyl ester (D1c)

Nitration of D1b was carried out using a solution of nitric acid and acetic anhydride; the crude product was purified by chromatography on silica gel using EtOAc/n-hexane as eluant to afford the title compound D1c. M$^+$–C(CH$_3$)$_3$ +2H=267

7-Amino-8-methoxy-1,2,4,5-tetrahydro-3-benzazepine-3-carboxylic acid tert-butyl ester (D1)

Hydrogenation of D1c at 50 psi in ethanol over 10% palladium on charcoal at room temperature afforded the title compound D1. MH$^+$ 293.

DESCRIPTION 2

7-Amino-1,2,4,5-tetrahydro-3-benzazepine-3-carboxylic acid tert-butyl ester (D2)

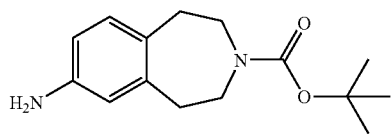

This compound was prepared using the procedure described in EP 284384 i.e.

7-Nitro-1,2,4,5-tetrahydro-3H-3-benzazepine (D2a)

1,2,4,5-Tetrahydro-3H-benzazepine (1 g) (See P. Ruggli et al., Helv. Chim. Acta, 18, 1388, [1935]) was added slowly dropwise to stirred fuming nitric acid (25 ml) at −10° C. Stirring was continued at −10° C. for 1 hour and the reaction mixture was then poured onto ice, the precipitate collected by filtration and dried to give the title compound as the nitrate salt, 1.4 g. This was suspended in water, cooled to 5° C. and neutralised with 5M sodium hydroxide. The precipitate was collected by filtration, recrystallised from water and dried, affording the title compound D1a as a white solid (0.6 g)

3-Tert-butoxycarbonyl-7-nitro-1,2,4,5-tetrahydro-3H-3-benzazepine (D2b)

A solution of di-t-butyidicarbonate (2.18 g) in dry dichloromethane (15 ml) was added dropwise to a stirred solution of 7-nitro-1,2,4,5-tetrahydro-3H-3-benzazepine (1.92 g) in dry dichloromethane (40 ml) at 0° C. After 18 h at room temperature the solvent was evaporated, giving an oil. This oil was dissolved in dichloromethane, washed twice with saturated aqueous sodium bicarbonate, three times with 1M hydrochloric acid and twice with brine. The organic solution was dried and evaporated giving an oil D2b, 2.33 g.

7-Amino-1,2,4,5-tetrahydro-3-benzazepine-3-carboxylic acid tert-butyl ester (D2)

A solution of 3-tert-butoxycarbonyl-7-nitro-1,2,4,5-tetrahydro-3H-3-benzazepine (2.1 g) was stirred under a hydrogen atmosphere (50 p.s.i.) in ethanol (40 ml) containing 5% Pd/C (0.21 g) for 3 hours. The catalyst was removed by filtration and the solvent evaporated to give the title compound D2 as a low-melting solid, 2.0 g. MH$^+$ 263

DESCRIPTION 3

Amino-dimethylamino-1,2,4,5-tetrahydro-benzo[d]azepine-3-carboxylic acid tert-butyl ester (D3)

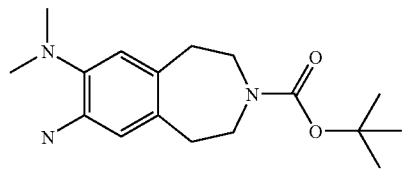

This compound was prepared according to the procedure described in WO 03/068752A1

DESCRIPTION 4

7-(5-Bromo-thiophene-2-sulfonylamino)-8-methoxy-1,2,4,5-tetrahydro-benzo[d]azepine-3-carboxylic acid tert-butyl ester (D4)

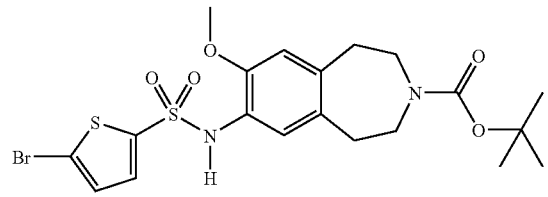

To an ice bath cooled solution of the methoxy aniline intermediate D1 (2.0 g, 0.0068 moles) in dry pyridine was added dropwise a solution of 5-bromothiophene-2-sulfonyl chloride (2.01 g, 0.0077 moles) in dichloromethane. The mixture was stirred for 1 hour at room temperature. The mixture was evaporated to dryness then purified by chromatography over silica, eluting with hexane up to 50% EtOAc/hexane, affording the title compound D4 as a white foam (3.18 g, 90%). M-H 517. ¹H NMR: δ CDCl₃ 1.48 (9H,s), 2.81 (4H, m), 3.49 (4H, m), 3.67 (3H, s), 6.60 (1H, s), 6.90 (1H, s), 6.94 (1H, d), 7.19 (1H, d), 7.30 (1H, s).

DESCRIPTION 5

7-(5-Bromo-thiophene-2-sulfonylamino)-1,2,4,5-tetrahydro-benzo[d]azepine-3-carboxylic acid tert-butyl ester (D5)

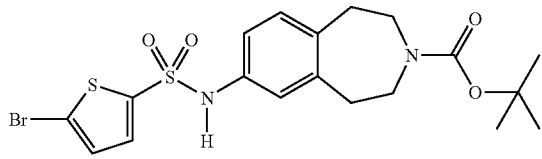

This compound was prepared using a similar procedure to that described for D4 above. MH⁺ 488.

DESCRIPTION 6

(5-Bromo-thiophene-2-sulfonylamino)-dimethylamino-1,2,4,5-tetrahydro-benzo[d]azepine-3-carboxylic acid tert-butyl ester (D6)

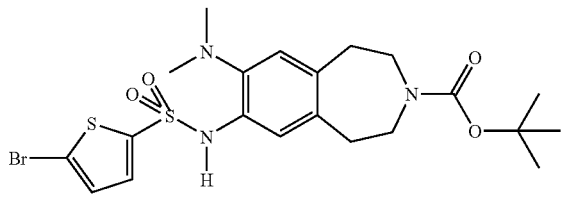

To an ice bath cooled solution of the intermediate D3 (2.0 g, 0.0065 moles) in dry pyridine was added dropwise a solution of 5-bromothiophene-2-sulfonyl chloride (1.88 g, 0.0072 moles) in dichloromethane. The mixture was stirred for 1 hour at room temperature. The mixture was evaporated to dryness then purified by chromatography over silica, eluting with hexane up to 50% EtOAc/hexane, affording the title compound D6 as a brown solid (2.1 g, 90%). M-H 532. ¹H NMR: δ $_{MeOD}$ 1.45 (9H,s), 2.76 (2H, m), 3.02 (2H, m), 3.30 (6H,s), 3.48 (2H, m), 3.58 (2H, m), 6.47 (1H, s), 7.26 (2H, m), 7.76 (1H, s).

DESCRIPTION 7

7-[5-(4-Chloro-phenyl)-thiophene-2-sulfonylamino]-8-methoxy-1,2,4,5-tetrahydro-benzo[d]azepine-3-carboxylic acid tert-butyl ester (D7)

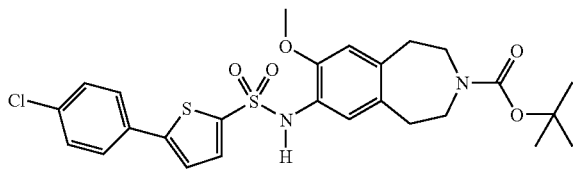

A solution of the bromo intermediate D5 (1.20 g, 0.0023 moles), 4-chlorophenylboronic acid (0.55 g, 0.0034 moles), K₂CO₃ (2M solution, 15 ml), ethanol (15 ml) and toluene (50 ml) at room temperature was degassed by bubbling argon through the solution for 10 minutes. Pd(PPh₃)₄ (0.4 g, 0.000375 moles) was added and the mixture heated at 60° C. under argon for 4 hours. Upon cooling the mixture was partitioned between water and ethyl acetate. The aqueous phase was re-extracted with ethyl acetate (×3) and the combined organic phase washed with water, brine then dried over anhydrous MgSO₄. The solution was evaporated to dryness then purified by chromatography over silica eluting, with hexane up to 50% EtOAc/hexane, affording the title compound D7 as a white foam (1.09 g, 86%). M-H 547. ¹H NMR: δ CDCl₃ 1.47 (9H, s) 2.83(4H, m), 3.50 (4H, m), 3.66 (3H,s), 6.55 (1H, s), 6.96 (1H, s), 7.12 (1H, d), 7.33–7.50 (5H, m).

DESCRIPTION 8

[5-(4-Chloro-phenyl)-thiophene-2-sulfonylamino]-dimethylamino-1,2,4,5-tetrahydro-benzo[d]azepine-3-carboxylic acid tert-butyl ester (D8)

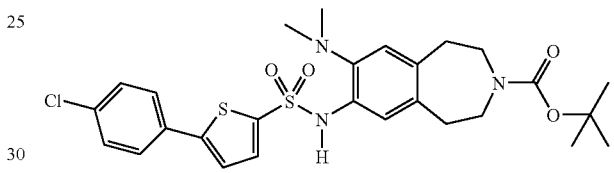

A solution of the bromo intermediate D6 (0.2 g, 0.00037 moles), 4-chlorophenylboronic acid (0.070 g, 0.00045 moles), K₂CO₃ (2M solution, 1 ml), ethanol (1 ml) and toluene (2 ml) at room temperature was degassed by bubbling argon through the solution for 10 minutes. Pd(PPh₃)₄ (0.1 g, 0.000086 moles) was added and the mixture heated at 60° C. under argon for 24 hours. Upon cooling the mixture was partitioned between water and ethyl acetate. The aqueous phase was re-extracted with ethyl acetate (×3) and the combined organic phase washed with water, brine then dried over anhydrous MgSO₄. The solution was evaporated to dryness then purified by chromatography over silica eluting, with hexane up to 50% EtOAc/hexane, affording the title compound D8 as a off white foam, which was used directly in the next step. M-H 563.

DESCRIPTION 9

5-(4-Chloro-phenyl)-thiophene-2-sulfonic acid (8-methoxy-2,3, 4,5-tetrahydro-1-H-benzo[d]azepin-7-yl)-amide (D9)

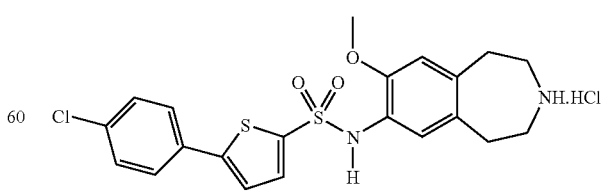

A solution of the Boc-protected amine D7 (1.05 g, 0.00199 moles) in 1.4-dioxane (20 ml) and 4M HCl in dioxane (10 ml) was stirred under argon at room temperature overnight. The resultant mixture was evaporated to dryness to give the hydrochloride salt of the title compound D9 as a cream solid (0.96 g, 100%). M-H 448.5. $^1$H NMR: δ DMSO-d$^6$ 3.08 (4H, m), 3.32 (4H, br s), 3.52 (3H, s), 6.85 (1H, s), 7.10 (1H, s), 7.41 (1H, d), 7.49–7.53 (3H, m), 7.69 (1H, s), 7.73 (1H, s), 9.27 (2H,br s), 9.74 (1 H, br s).

DESCRIPTION 10

5-(4-Chloro-phenyl)-thiophene-2-sulfonic acid (8-dimethylamino-2,3, 4,5-tetrahydro-1-H-benzo[d]azepin-7-yl)-amide (D10)

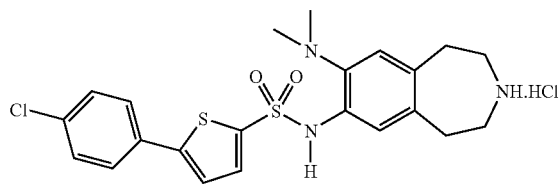

A solution of the intermediate D8 in methanol (1 ml) and 4M HCl in dioxane (5 ml) was stirred under argon at room temperature overnight. The resultant mixture was evaporated to dryness to give the hydrochloride salt of the title compound D10 as a off white foam, which was used directly in the next step. M-H 463.

EXAMPLE 1

5-(4-Chloro-phenyl)-thiophene-2-sulfonic acid (8-methoxy-3-methyl-2,3,4,5-tetrahydro-1-H-benzo[d]azepin-7-yl)-amide (E1)

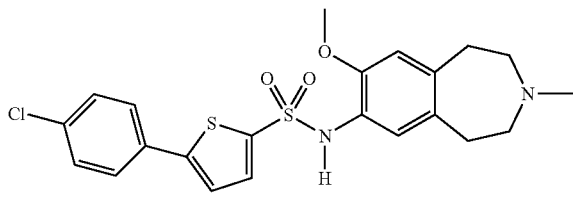

To a suspension of the amine hydrochloride salt D9 (0.96 g, 0.00198 moles) in 1,2-dichloroethane (50 ml) at room temperature was added triethylamine (5 ml, excess) followed by 37% aqueous formaldehyde (5 ml, excess). After vigorous stirring for 5 minutes, sodium triacetoxyborohydride (5 g, excess) was added portionwise over 5 minutes and the resultant solution stirred for a further 2 hours. The reaction was partitioned between water and dichloromethane and the organic phase washed with water, brine and dried over anhydrous MgSO$_4$. The solution was evaporated to dryness affording the title compound E1 as a pale yellow solid (0.993 g, 100%). M-H 461. $^1$H NMR: δ CDCl$_3$ 2.67–2.88 (6H, m), 3.60–3.95 (8H, m), 6.58 (1H, s), 7.07 (1H, S), 7.13 (1H, d), 7.33–7.50 (6H, m).

Examples 2–12 were prepared using analogous procedures to Example 1 using the appropriate starting materials, with the products being isolated as either free bases or hydrochloride salts. Examples 13 to 15 were prepared using analogous procedures to those described in Descriptions 3, 4, 6 and Example 1 from the commercially available sulfonyl chlorides with the products being isolated as either free bases or hydrochloride salts. All $^1$H NMR are consistent with the structures shown.

EXAMPLE 16

5-(4-Chloro-phenyl)-thiophene-2-sulfonic acid (dimethylamino-methyl-2,3,4,5-tetrahydro-1-H-benzo[d]azepin-7-yl)-amide (E16)

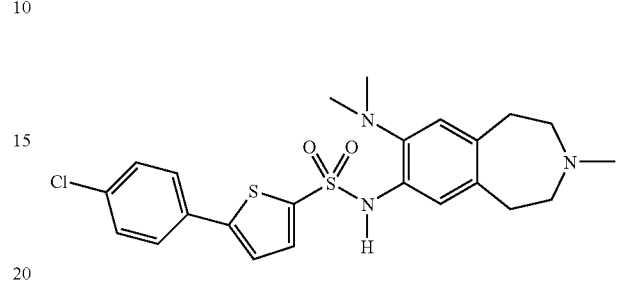

To a suspension of the intermediate D10, in 1,2-dichloroethane (1 ml) at room temperature was added triethylamine (0.3, excess) followed by 37% aqueous formaldehyde (0.2, excess). After vigorous stirring for 5 minutes, sodium triacetoxyborohydride (100 mg, excess) was added portionwise over 5 minutes and the resultant solution stirred for a further 2 hours. The reaction was partitioned between water and dichloromethane and the organic phase washed with water, brine and dried over anhydrous MgSO$_4$. The solution was evaporated to dryness affording the title compound E16 as a pale yellow solid (20 mg, 99% ). M-H 477. $^1$H NMR: δ CDCl$_3$ 2.36 (3H, s), 2.44 (6H, s), 2.54 (4H, m), 2.84 (2H, m), 2.91 (2H, m), 6.87 (1H, s), 7.12 (1H, d), 7.33–7.51 (6H, m).

Examples 17–19 were prepared using analogous procedures to Example 16 using the appropriate starting materials, with the products being Isolated as either free bases or hydrochloride salts. All $^1$H NMR are consistent with the structures shown.

All the compounds listed below in Table 1 relate to compounds of formula (IJ):

TABLE 1

(IJ)

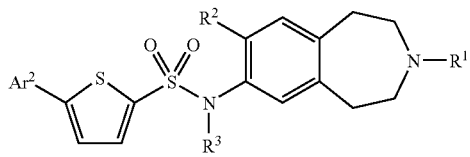

| Example | R$^1$ | R$^2$ | R$^3$ | Ar$^4$ | MH$^+$ |
|---|---|---|---|---|---|
| 1 | Me | MeO | H | 4-chlorophenyl | 461 |
| 2 | Me | MeO | H | 3-methoxyphenyl | 459 |
| 3 | Me | MeO | H | 4-methoxyphenyl | 459 |
| 4 | Me | MeO | H | 3,4-difluorophenyl | 465 |
| 5 | Me | MeO | H | 2,4-difluorophenyl | 465 |
| 6 | Me | MeO | H | 3-chlorophenyl | 463 |
| 7 | Me | MeO | H | 3-fluorophenyl | 447 |
| 8 | Me | MeO | H | 4-trifluoromethylphenyl | 497 |
| 9 | Me | MeO | H | 3-trifluoromethylphenyl | 497 |
| 10 | Me | MeO | H | 4-fluorophenyl | 447 |
| 11 | Me | H | H | 4-fluorophenyl | 417 |
| 12 | Me | H | H | 4-chlorophenyl | 433 |
| 13 | Me | MeO | H | 3-isoxazolyl | 404 |
| 14 | Me | MeO | H | 2-methyl-thiazol-5-yl | 450 |
| 15 | Me | H | H | 3-thienyl | 405 |

TABLE 1-continued

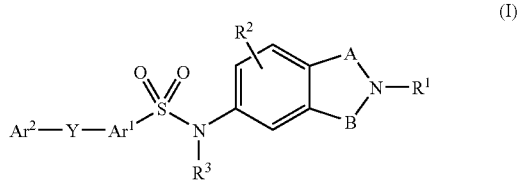

| Example | R¹ | R² | R³ | Ar⁴ | MH⁺ |
|---------|-----|------|-----|-------------------|-----|
| 16 | Me | NMe₂ | H | 4-chlorophenyl | 477 |
| 17 | Me | NMe₂ | H | 4-fluorophenyl | 460 |
| 18 | Me | NMe₂ | H | 2,4-difluorophenyl | 478 |
| 19 | Me | NMe₂ | H | 3,4-difluorophenyl | 478 |

All publications, including but not limited to patents and patent applications, cited in this specific are herein incorporated by reference as if each individual publication were specifically and individually indicated to be incorporated by reference herein as though fully set forth.

The invention claimed is:

1. A compound of formula (I):

$$\text{Ar}^2-\text{Y}-\text{Ar}^1-\underset{\underset{R^3}{|}}{\overset{\overset{O\ \ O}{\underset{\|}{\underset{\|}{S}}}}{\phantom{-}}}-N-\phantom{-}$$

wherein

A and B represent the groups —(CH$_2$)$_m$— and —(CH$_2$)$_n$— respectively;

R$^1$ represents C$_{1-6}$alkyl;

R$^2$ represents hydrogen, halogen, hydroxy, cyano, nitro, hydroxyC$_{1-6}$alkyl, trifluoromethyl, trifluoromethoxy, C$_{1-6}$alkyl, C$_{1-6}$alkoxy, —(CH$_2$)$_p$C$_{3-6}$cycloalkyl, —(CH$_2$)$_p$OC$_{3-6}$cycloalkyl, —COC$_{1-6}$alkyl, —SO$_2$C$_{1-6}$alkyl, —SOC$_{1-6}$alkyl, —S—C$_{1-6}$alkyl, —CO$_2$C$_{1-6}$alkyl, —CO$_2$NR$^4$R$^5$, —SO$_2$NR$^4$R$^5$, —(CH$_2$)$_p$NR$^4$R$^5$, —(CH$_2$)$_p$NR$^4$COR$^5$, an optionally substituted aryl group, an optionally substituted heteroaryl group or an optionally substituted heterocyclyl group;

R$^3$ represents hydrogen or C$_{1-6}$alkyl;

Ar$^1$ represents an optionally substituted heteroaryl group;

Ar$^2$ represents an optionally substituted phenyl or an optionally substituted heteroaryl group;

Y represents a bond, —O—, —C$_{1-6}$alkyl-, —CR$^6$R$^7$X—, —XCR$^6$R$^7$—, —NR$^8$CO— or —CONR$^8$—;

X represents oxygen, sulfur, —SO— or —SO$_2$—;

R$^4$ and R$^5$ each independently represent hydrogen or C$_{1-6}$alkyl or, together with the nitrogen or other atoms to which they are attached, form an azacycloalkyl ring or an oxo-substituted azacycloalkyl ring;

R$^6$ and R$^7$ each independently represent hydrogen, C$_{1-6}$alkyl or fluoro;

R$^8$ represents hydrogen or C$_{1-6}$alkyl;

m and n independently represent an integer selected from 1 and 2;

p independently represents an integer selected from 0, 1, 2 and 3;

or a pharmaceutically acceptable salt, solvate or pharmaceutically acceptable derivative thereof.

2. A compound of formula (I) which is 5-(4-Chlorophenyl)-thiophene-2-sulfonic acid (8-methoxy-3-methyl-2,3,4,5-tetrahydro-1H-benzo[d]azepin-7-yl)amide;

5-(3-Methoxyphenyl)-thiophene-2-sulfonic acid (8-methoxy-3-methyl-2,3,4,5-tetrahydro-1H-benzo[d]azepin-7-yl)amide;

5-(4-Methoxyphenyl)-thiophene-2-sulfonic acid (8-methoxy-3-methyl-2,3,4,5-tetrahydro-1H-benzo[d]azepin-7-yl)amide;

5-(3,4-Difluorophenyl)-thiophene-2-sulfonic acid (8-methoxy-3-methyl-2,3,4,5-tetrahydro-1H-benzo[d]azepin-7-yl)amide;

5-(2,4-Difluorophenyl)-thiophene-2-sulfonic acid (8-methoxy-3-methyl-2,3,4,5-tetrahydro-1H-benzo[d]azepin-7-yl)amide;

5-(3-Chlorophenyl)-thiophene-2-sulfonic acid (8-methoxy-3-methyl-2,3,4,5-tetrahydro-1H-benzo[d]azepin-7-yl)amide;

5-(3-Fluorophenyl)-thiophene-2-sulfonic acid (8-methoxy-3-methyl-2,3,4,5-tetrahydro-1H-benzo [d]azepin-7-yl)amide;

5-(4-Trifluoromethylphenyl)-thiophene-2-sulfonic acid (8-methoxy-3-methyl-2,3,4,5-tetrahydro-1H-benzo[d]azepin-7-yl)amide;

5-(3-Trifluoromethylphenyl)-thiophene-2-sulfonic acid (8-methoxy-3-methyl-2,3,4,5-tetrahydro-1H-benzo[d]azepin-7-yl)amide;

5-(4-Fluorophenyl)-thiophene-2-sulfonic acid (8-methoxy-3-methyl-2,3,4,5-tetrahydro-1H-benzo[d]azepin-7-yl)amide;

5-(4-Fluorophenyl)-thiophene-2-sulfonic acid (3-methyl-2,3,4,5-tetrahydro-1H-benzo[d]azepin-7-yl)amide;

5-(4-Chlorophenyl)-thiophene-2-sulfonic acid (3-methyl-2,3,4,5-tetrahydro-1H-benzo[d]azepin-7-yl)amide;

5-(4-Chloro-2-methylphenyl)-thiophene-2-sulfonic acid (2,3,4,5-tetrahydro-1H-benzo[d]azepin-7-yl)-amide;

5-Isoxazol-3-yl-thiophene-2-sulfonic acid (8-methoxy-3-methyl-2,3,4,5-tetrahydro-1H-benzo [d]azepin-7-yl)-amide;

5-(2-Methylthiazol-5-yl)-thiophene-2-sulfonic acid (8-methoxy-3-methyl-2,3,4,5-tetrahydro-1H-benzo[d]azepin-7-yl)-amide;

[2,3']Bithiophenyl-5-sulfonic acid (2,3,4,5-tetrahydro-1H-benzo[d]azepin-7-yl)-amide;

[2,3']Bithiophenyl-5-sulfonic acid (3-methyl-2,3,4,5-tetrahydro-1H-benzo[d]azepin-7-yl)-amide;

5-(4-Chlorophenyl)thiophene-2-sulfonic acid (8-dimethylamino-3-methyl-2,3,4,5-tetrahydro-1H-3-benzazepin-7-yl)amide;

5-(4-Fluorophenyl)thiophene-2-sulfonic acid (8-dimethylamino-3-methyl-2,3,4,5-tetrahydro-1H-3-benzazepin-7-yl)amide;

5-(2,4-Difluorophenyl)thiophene-2-sulfonic acid (8-dimethylamino-3-methyl-2,3,4,5-tetrahydro-1H-3-benzazepin-7-yl)amide; and 5-(3,4-Difluorophenyl)thiophene-2-sulfonic acid (8-dimethylamino-3-methyl-2,3,4,5-tetrahydro-1H-3 -benzazepin-7-yl)amide.

3. A pharmaceutical composition comprising a compound of formula (I) as claimed in claim 1 or a pharmaceutically acceptable derivative thereof and a pharmaceutically acceptable carrier therefor.

* * * * *